United States Patent
Goble et al.

(10) Patent No.: US 6,984,231 B2
(45) Date of Patent: Jan. 10, 2006

(54) ELECTROSURGICAL SYSTEM

(75) Inventors: Coliin C. O. Goble, Surrey (GB); Scott T. Latterell, Minneapolis, MN (US); Douglas S. Wahnschaffe, Otsego, MN (US)

(73) Assignee: Gyrus Medical Limited, Cardiff (GB)

( * ) Notice: Subject to any disclaimer, the term of this patent is extended or adjusted under 35 U.S.C. 154(b) by 163 days.

(21) Appl. No.: 10/228,284

(22) Filed: Aug. 27, 2002

(65) Prior Publication Data

US 2003/0073990 A1 Apr. 17, 2003

Related U.S. Application Data

(60) Provisional application No. 60/314,650, filed on Aug. 27, 2001.

(30) Foreign Application Priority Data

May 27, 2002 (GB) .............................................. 0212162

(51) Int. Cl.
*A61B 18/14* (2006.01)

(52) U.S. Cl. ............................. 606/37; 606/42; 606/48; 606/51

(58) Field of Classification Search .................. 606/37, 606/41, 42, 45, 48–51
See application file for complete search history.

(56) References Cited

U.S. PATENT DOCUMENTS

| | | | |
|---|---|---|---|
| 5,160,334 A | | 11/1992 | Billings et al. |
| 6,174,309 B1 | * | 1/2001 | Wrublewski et al. .......... 606/45 |
| 6,416,509 B1 | | 7/2002 | Goble et al. |
| 6,679,882 B1 | * | 1/2004 | Kornerup ...................... 606/51 |
| 2003/0073990 A1 | | 4/2003 | Goble et al. |
| 2004/0006340 A1 | * | 1/2004 | Latterell et al. ............... 606/48 |

FOREIGN PATENT DOCUMENTS

| | | |
|---|---|---|
| DE | 199 43 792 A1 | 2/2001 |
| WO | WO 96/37156 A1 | 11/1996 |
| WO | WO 98/38932 A1 | 9/1998 |

OTHER PUBLICATIONS

International Search Report in International Application No. PCT/GB2004/000917, Oct. 6, 2004, pp. 1–2.

* cited by examiner

*Primary Examiner*—Lee S. Cohen
(74) *Attorney, Agent, or Firm*—Nixon & Vanderhye P.C.

(57) ABSTRACT

An electrosurgical system includes a generator (10) for generating radio frequency power, and an electrosurgical instrument (12) including at least three electrodes. The generator comprises a radio frequency output stage having at least a pair of output lines (60C), and a power supply (66) coupled to the output stage for supplying power to the output stage. The generator also includes a controller (72) capable of varying a radio frequency signal supplied to the output lines, and a switching circuit (62) having three or more output connections (62A, 62B, 62C) each electrically connected with a respective one of the at least three electrodes. This switching circuit is operable to vary the connections between the output lines (60C) and the output connections (62A, 62B, 62C). A switching device (16A, 16B) forming part of the system is operable by the user to send a signal to the switching circuit (62) within the generator in order to vary the electrode or electrodes to which radio frequency power is supplied, the switching device also causing a signal to be sent to the controller (72) such that the radio frequency signal supplied to at least one of the three or more output connections varies depending on the electrode or electrodes to which radio frequency power is supplied. In one arrangement of the switching circuit, one of the electrodes has no direct connection to the output stage of the generator and is connected via a capacitor to another of the electrodes.

16 Claims, 6 Drawing Sheets

ELECTROSURGICAL SYSTEM

Figure 1:
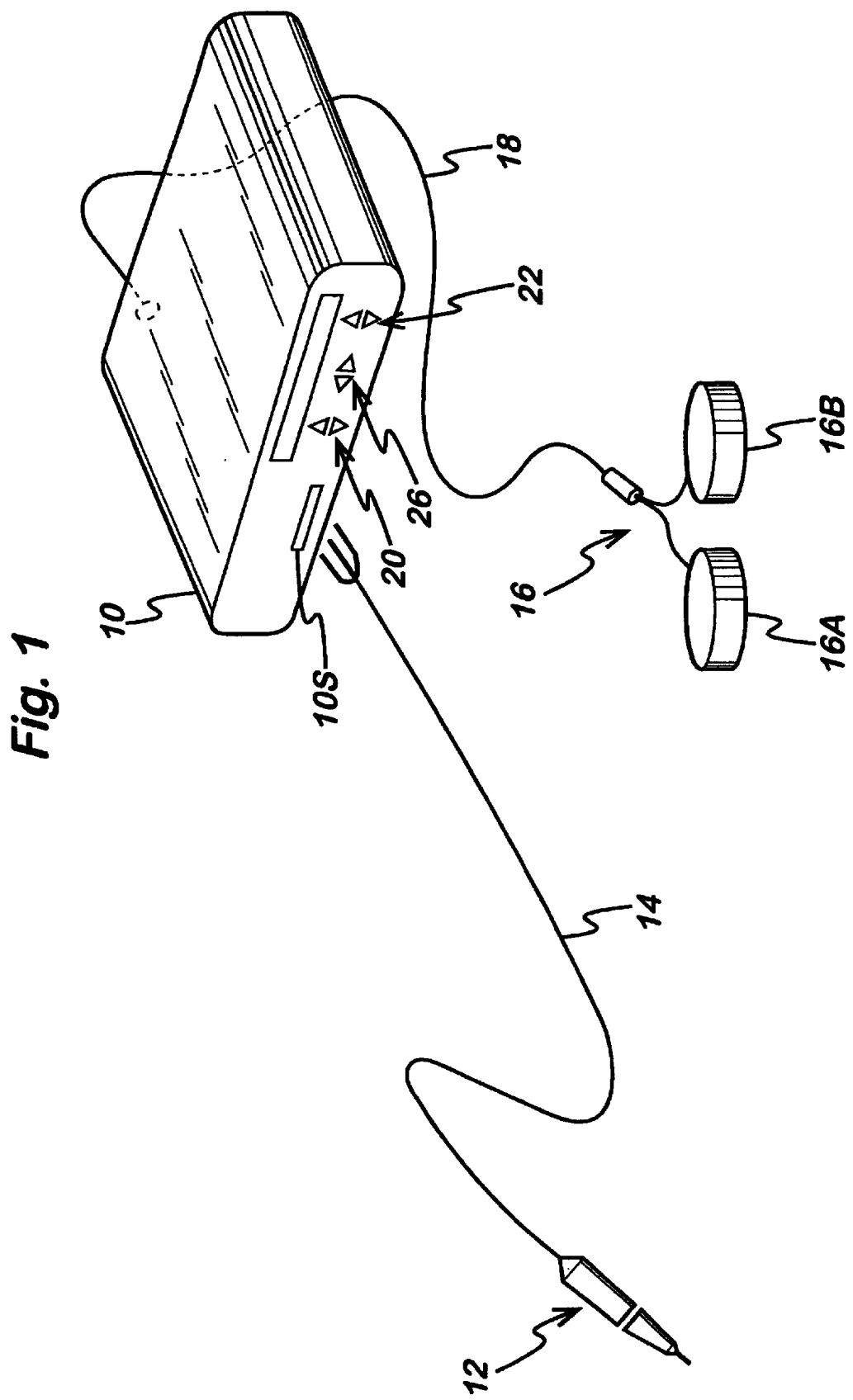

This application claims the benefit of U.S. Provisional Application No. 60/314,650, filed Aug. 27, 2001, the entire content of which is hereby incorporated by reference in this application.

This invention relates to an electrosurgical system comprising an electrosurgical generator and a handpiece including electrosurgical electrodes. Such systems are commonly used for the cutting and/or coagulation of tissue in surgical intervention, most commonly in "keyhole" or minimally invasive surgery, but also in laparoscopic or "open" surgery.

It is known to provide electrosurgical generators which provide different radio frequency signals for cutting and coagulation, and also to switch between two different instruments, e.g. bipolar and monopolar instruments. In a first type of prior art system, it is also known to provide an electrosurgical instrument with a single electrode, and switching means on the instrument to connect the electrode alternately to either a cutting output or to a coagulating output from the generator. Examples of this type of instrument are to be seen in U.S. Pat. No. 4,427,006, U.S. Pat. No. 5,376,089 and U.S. Pat. No. 5,573,424.

Alternatively, in a second type of prior art system, it is known to provide an instrument with multiple electrodes, and to provide switching means on the instrument to be able to connect the signal from the generator to different electrodes or combinations of electrodes. Examples of this type of instrument are to be seen in U.S. Pat. No. 5,269,780 and U.S. Pat. No. 5,951,551. The disadvantage of all of these prior art systems is that it is not possible to optimize both the signal supplied by the generator and the choice of electrodes. In the case of the first type of prior art system, the use of a single electrode means that its design must always be a compromise between designs suited to cutting and those suited to coagulation. In the case of the second type of prior art, the instrument uses the same output signal from the generator for whichever combination of electrodes is deployed. U.S. Pat. No. 6,270,497 discloses a device which switches between coagulation and cutting operations, but which is relatively complicated in design.

It is an object of the present invention to provide an electrosurgical system which attempts to provide an optimized combination of electrodes in the handpiece, and electrosurgical signal from the generator, and which is relatively simple in operation.

Accordingly there is provided an electrosurgical system including a generator for generating radio frequency power, and an electrosurgical instrument including at least three electrodes, the generator comprising (i) a radio frequency output stage having at least a pair of radio frequency output lines, (ii) a power supply coupled to the output stage for supplying power to the output stage, (iii) a controller capable of varying a radio frequency signal supplied to the radio frequency output lines, and (iv) a switching circuit having at least three output connections, each in electrical connection with a respective one of the at least three electrodes and operable to vary the connections between the radio frequency output lines and the three or more output connections, characterised in that the system further includes a switching device operable to send a signal to the switching circuit within the generator in order to vary the electrode or electrodes to which radio frequency power is supplied, the switching device also causing a signal to be sent to the controller such that the radio frequency signal supplied to at least one of the three or more output connections varies depending on the electrode or electrodes to which radio frequency power is supplied, one arrangement of the switching circuit being such that one of the electrodes has no direct connection to the output stage of the generator and is connected via a capacitor to another of the electrodes.

The capacitor preferably has a value of between 1 and 10 nF. This arrangement can simplify the switching required within the generator, and/or free up additional switching capability within the generator for use in other circumstances.

In this way, the electrosurgical signal employed can be optimised depending on the choice of electrodes, and similarly the electrodes can be designed specifically for the function they are chosen to perform. Preferably, the controller automatically adjusts the radio frequency power supplied to at least one of the three or more output connections to limit the peak generator output voltage to at least a first value when a first combination of electrodes is selected by the switching circuit, and to at least a second value when a second combination of electrodes is selected by the switching circuit.

In one arrangement, the generator supplies radio frequency (RF) power to at least three electrodes simultaneously, the output voltage being limited to a first peak value between a first combination of electrodes, and to a second peak value between a second combination of electrodes. This can be achieved by the generator having first and second output stages adapted to produce RF power for the first and second combination of electrodes respectively. Alternatively, and more simply, at least three of the electrodes are connected to respective other electrodes by capacitors, such that the peak voltage delivered by a single output stage is different between the first and second combination of electrodes.

In one arrangement two of the three or more electrodes are in the form of jaws adapted to grasp tissue therebetween, and the third electrode is mounted on one of the jaws, separated therefrom by an insulating member. The third electrode may be mounted on the internal or external face of one of the jaws, or even at the tip thereof. The third electrode may be mounted on one of the jaws in a recess therein, such that only a part of the electrode protrudes from the jaw. This type of arrangement applies to forceps or scissors-type instruments, suitable for grasping and/or cutting tissue.

Alternatively, at least one and preferably at least three of the electrodes is in the form of a hook. Hook and needle-type instruments are also common in Laparoscopic surgery, and may be employed in the present invention. Conveniently one of the hook electrodes extends distally beyond the other electrodes. Preferably the electrode which extends distally beyond the other electrodes is positioned centrally between the other electrodes.

In one construction at least one of the electrodes is longitudinally movable such that it can be extended and retracted with respect to the other electrodes. In this way tissue can be held in the gap formed between the retractable electrode and the other electrodes. As before, the longitudinally movable electrode is preferably positioned centrally between the other electrodes.

Figure 2:
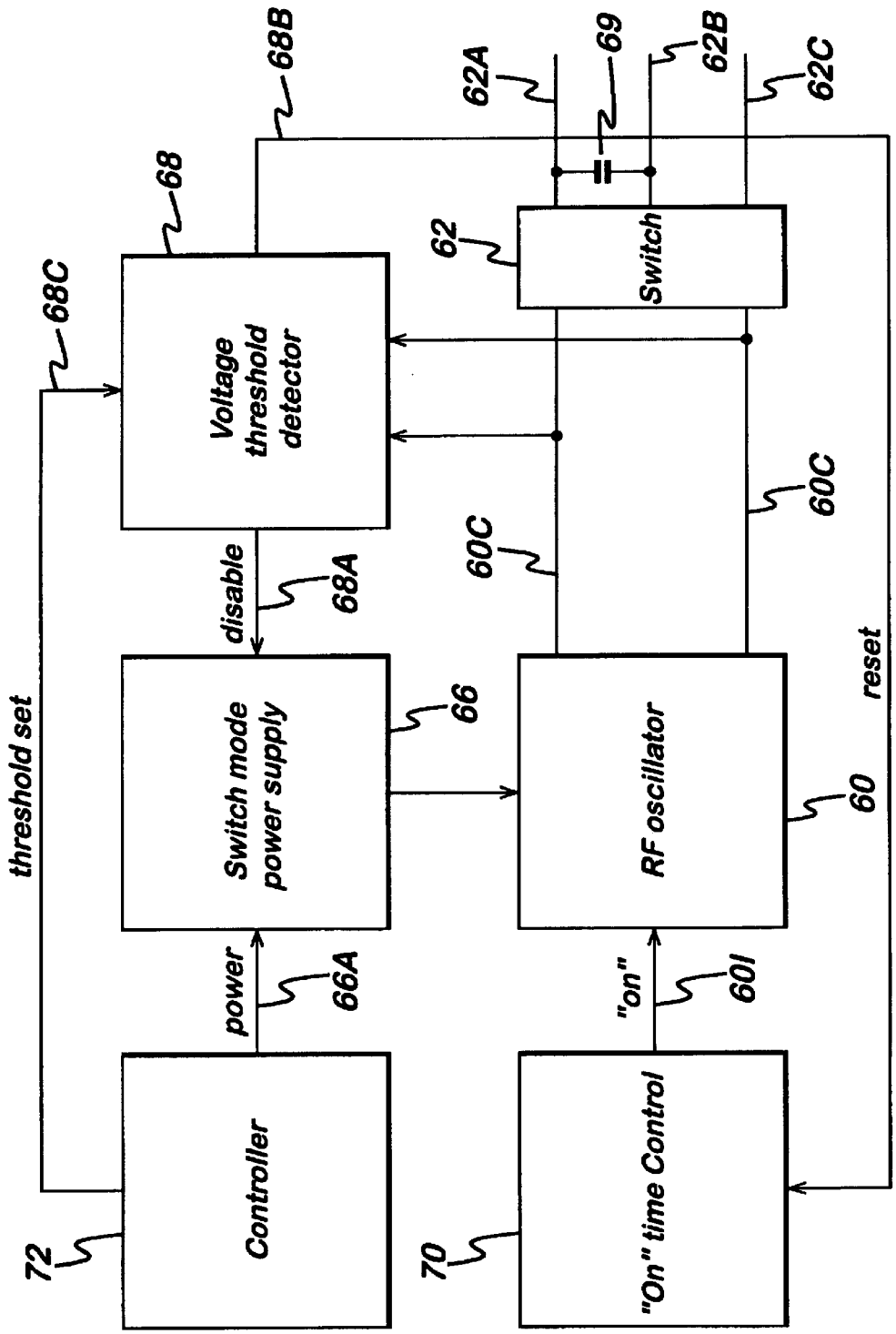
Figure 3:
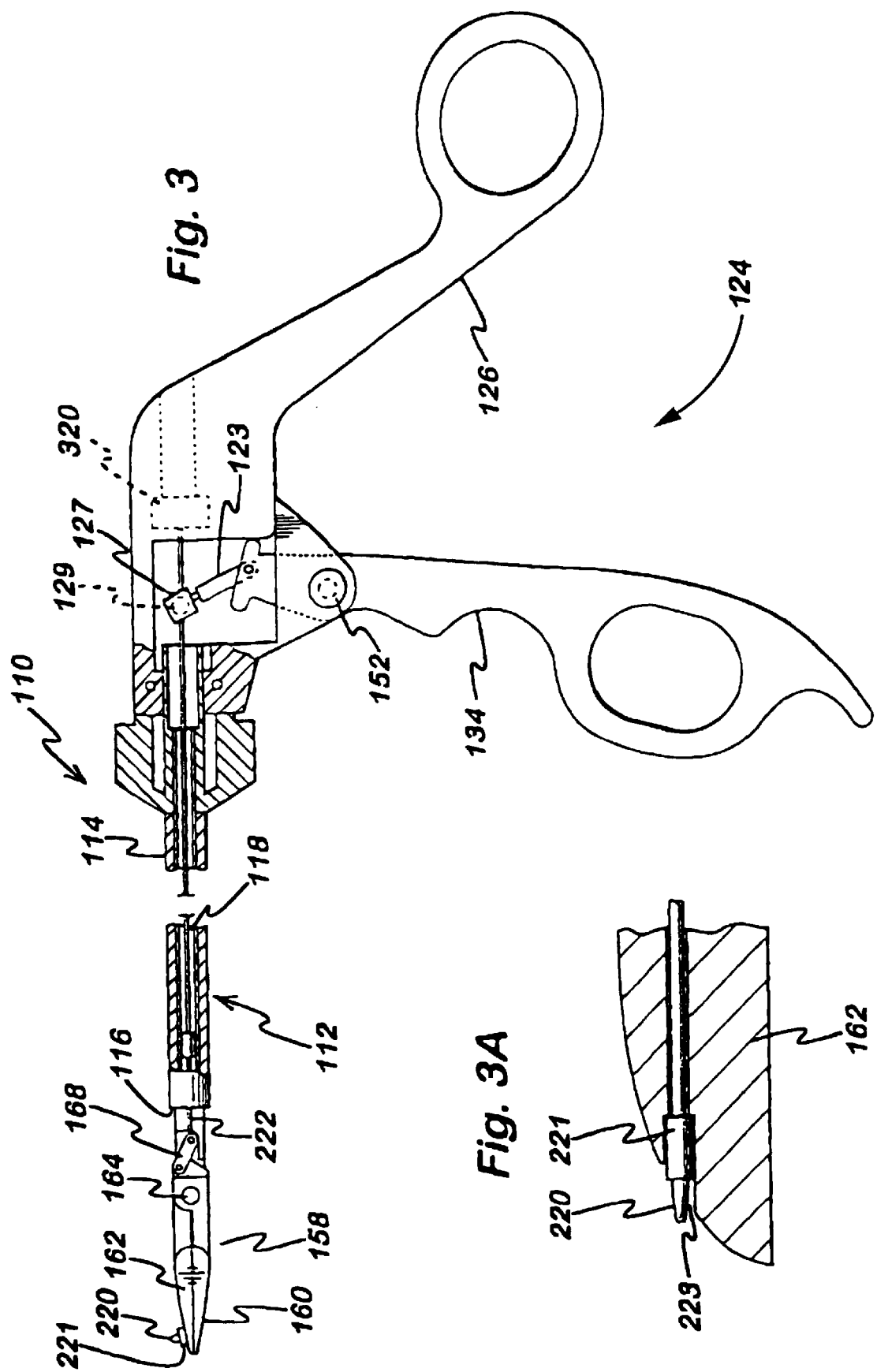
Figure 4:
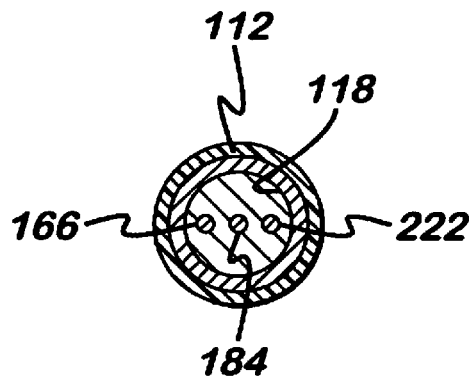
Figure 5A:
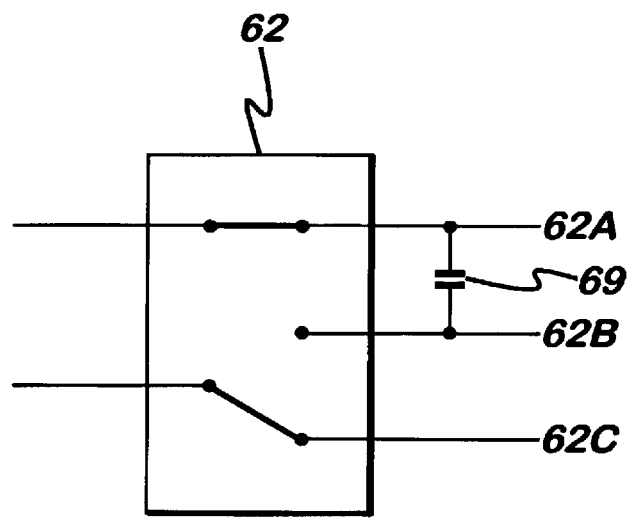
Figure 5B:
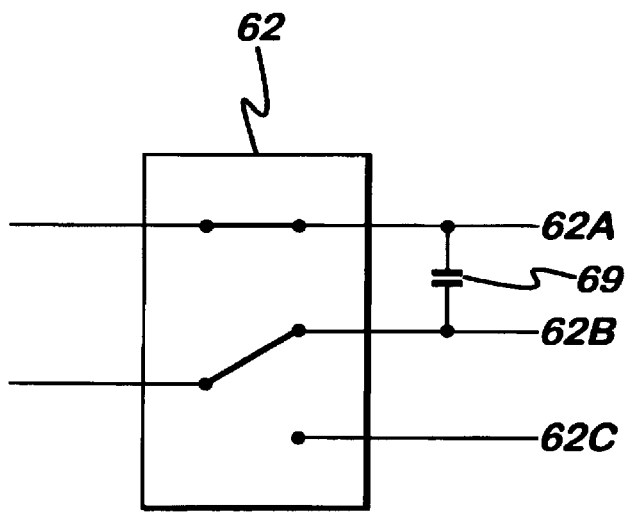
Figure 6:
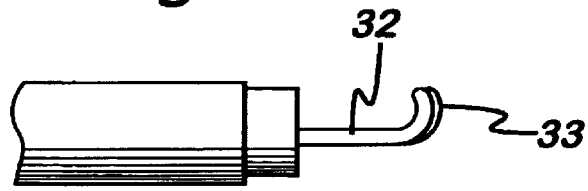
Figure 7:
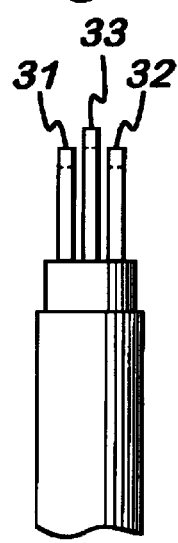
Figure 7A:
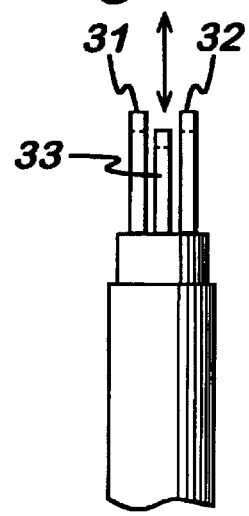
Figure 8:
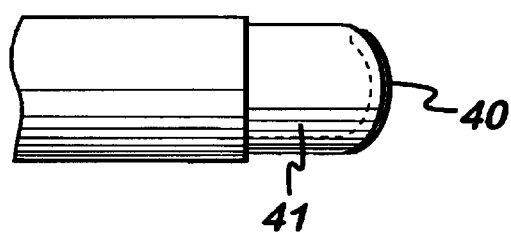
Figure 9:
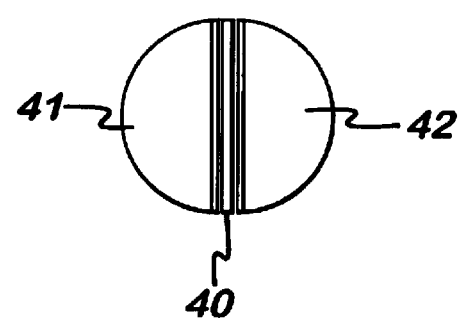
Figure 10:
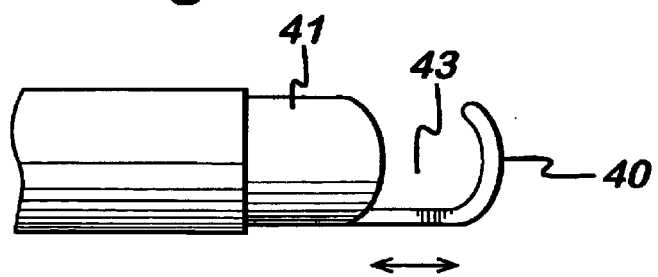
Figure 11A:
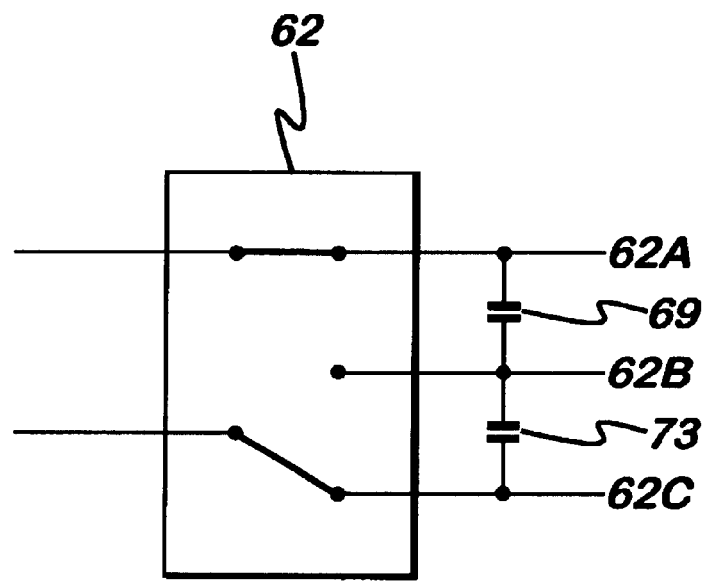
Figure 11B:
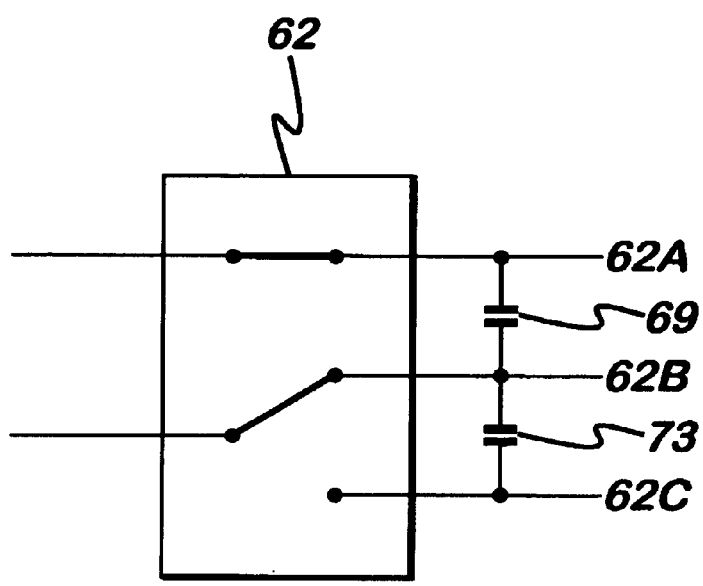

The invention will now be further described, by way of example only, with reference to the accompanying drawings, in which:

FIG. 1 is a schematic diagram of an electrosurgical system in accordance with the present invention, FIG. 2 is a block diagram of a generator forming part of the system of FIG. 1, FIG. 3 is a schematic side view, shown partly in section, of a forceps-type instrument for use in the system of FIG. 1, FIG. 3*a* is a sectional side view showing an alternative embodiment of jaw for the instrument of FIG. 3, FIG. 4 is a cross-sectional view through the shafting of the instrument of FIG. 3, FIGS. 5A and 5B are schematic views of the switching circuitry of FIG. 2, shown in first and second alternative conditions, FIGS. 6 and 7 are side and plan views, respectively, of a part of an alternative instrument for use in the system of FIG. 1, FIG. 7*a* is a plan view of an alternative embodiment of the instrument of FIGS. 6 and 7, FIG. 8 is a side view of a part of a further alternative instrument for use in the system of FIG. 1, the instrument being shown with a movable electrode in a retracted position, FIG. 9 is an end view of the instrument of FIG. 8, FIG. 10 is a side view of the instrument of FIG. 8, shown with the movable electrode in an extended position, and FIGS. 11A and 11B are schematic circuit diagrams showing an alternative embodiment of a system in accordance with the invention.

Referring to FIG. 1, a generator 10 has an output socket 10S providing a radio frequency (RF) output for an instrument 12 via a connection cord 14. Activation of the generator may be performed from the instrument 12 via a connection in cord 14 or by means of a footswitch unit 16, as shown, connected to the rear of the generator by a footswitch connection cord 18. In the illustrated embodiment footswitch unit 16 has two footswitches 16A and 16B for selecting a coagulation mode and a cutting mode of the generator respectively. The generator front panel has push buttons 20 and 22 for respectively setting coagulation and cutting power levels, which are indicated in a display 24. Push buttons 26 are provided as an alternative means for selection between coagulation and cutting modes.

Referring to FIG. 2, the generator comprises a radio frequency (RF) output stage in the form of a power oscillator 60 having a pair of output lines 60C for coupling via switching circuit 62 to the instrument 12. Switching circuit 62 has three output connections 62A, 62B and 62C for connection to the electrodes of the instrument as will be described later. A capacitor 69 is connected between output connections 62A and 62B as shown. Power is supplied to the oscillator 60 by a switched mode power supply 66.

In the preferred embodiment, the RF oscillator 60 operates at about 400 kHz, with any frequency from 300 kHz upwards into the HF range being feasible. The switched mode power supply typically operates at a frequency in the range of from 25 to 50 kHz. Coupled across the output lines 60C is a voltage threshold detector 68 having a first output 68A coupled to the switched mode power supply 16 and a second output 68B coupled to an "on" time control circuit 70. A micro-processor controller 72 coupled to the operator controls and display (shown in FIG. 1) is connected to a control input 66A of the power supply 66 for adjusting the generator output power by supply voltage variation and to a threshold-set input 68C of the voltage threshold detector 68 for setting peak RF output voltage limits.

In operation, the microprocessor controller 72 causes power to be applied to the switched mode power supply 66 when electrosurgical power is demanded by the surgeon operating an activation switch arrangement which may be provided on a hand-piece or footswitch (see FIG. 1). A constant output voltage threshold is set independently of the supply voltage via input 68C according to control settings on the front panel of the generator (see FIG. 1). Typically, for desiccation or coagulation the threshold is set at a desiccation threshold value between 150 volts and 200 volts. When a cutting or vaporisation output is required the threshold is set to a value in the range of from 250 or 300 volts to 600 volts. These voltage values are peak values. Their being peak values means that for desiccation at least it is preferable to have an output RF wave-form of low crest factor to give maximum power before the voltage is clamped at the values given. Typically a crest factor of 1.5 or less is achieved.

When the generator is first activated, the status of the control input 60I of the RF oscillator 60 (which is connected to the "on" time control circuit 70) is "on", such that the power switching device which forms the oscillating element of the oscillator 60 is switched on for a maximum conduction period during each RF oscillation cycle. The power delivered to the load (not shown) depends partly on the supply voltage applied to the RF oscillator 60 from the switched mode power supply 66 and partly on the load impedance. The voltage threshold for a desiccation output is set to cause trigger signals to be sent to the "on" time control circuit 70 and to the switched mode power supply 66 when the voltage threshold is reached. The "on" time control circuit 70 has the effect of virtually instantaneously reducing the "on" time of the RF oscillator-switching device. Simultaneously, the switched mode power supply is disabled so that the voltage supplied to oscillator 60 begins to fall. The operation of the generator in this way is described in detail in our European Patent Application No. 0754437, the disclosure of which is hereby incorporated by way of reference.

FIG. 3 shows one type of instrument 12 which can be connected to the generator 10. The device is a bipolar forceps shown generally at 110. The forceps has an elongated tubular shaft 112 with a proximal end 114, distal end 116, and a lumen 118 which extends for the entire length of the shaft. At the proximal end 114 of the tubular shaft member 112 is a scissors-type handle assembly 124 with a first handle 126 and a second handle 134. The second handle 134 is pivotable with respect to the first, about pivot pin 152. In a known design of actuation mechanism, the second handle 134 has a pin 123 affixed to the top thereof, such that movement of the handle causes a corresponding movement of a sphere 129 supported in a U-shaped cradle 127.

Fitted into the distal end 116 of the shaft 112 is a forceps jaw assembly 158 comprising a first jaw member 160 and a second jaw member 162, pivotally joined to each other by an insulated rivet 164. Jaw member 162 is provided with a cutting electrode 220, isolated from jaw member 162 by a ceramic insulator 221. As shown in FIG. 4, three rigid electrically conductive rods 166, 184 and 222, each covered with a layer of electrical insulation, extend through the lumen 118 of the tubular member 112. The rods 166, 184 are pivotally connected to the respective jaw members 160, 162 by rigid links 168, whilst rod 222 is connected by means of a wire (not shown) to the electrode 220. The proximal ends of the rods 166, 184 and 222 extend from the shaft through the sphere 129 and terminate in a connector 320. Output connections 62A, 62B and 62C from the generator 10 are thereby electrically connected to the rods 166, 184 and 222 respectively, via lead 14 and connector 320.

The operation of the instrument will now be described. When it is desired to operate the instrument 12 in a cutting mode, footswitch 16A is depressed which causes a signal to be sent to the controller 72 which sets the switching circuit 62 its "cut" position. This is illustrated in FIG. 5A, in which the signals from the oscillator 60 are connected between output connections 62A and 62C. This means that the RF signal is applied between the cutting electrode 220 (via rod 222) and the jaw member 160 (via rod 166). Output connection 62B (and hence rod 184 and jaw member 162) has no direct connection to the generator, being connected solely via capacitor 69 to output connection 62A. The value of the capacitor 69 is typically 2.2 nF, and this is such that, in cutting mode, the output connection 62B is allowed to reach a similar potential to that of connection 62A.

At the same time as the controller 72 sets the switching circuit to the position in FIG. 5A, it also sends a signal via line 68C to the voltage threshold detector 68 to set the peak output voltage limit to a relatively high "cutting" level. The control of this cutting signal is described in more detail in EP 0754437, referred to earlier. In cutting mode, the output from the generator is a relatively high voltage, with a consequent low current level, and the impedance offered by the capacitor 69 is small in comparison with the impedance provided between the cutting electrode and the tissue being treated.

Alternatively, when it is desired to operate the instrument 12 in a coagulation mode, footswitch 16B is depressed which causes the controller 72 to set the switching circuit 62 to its "coag" state, as illustrated in FIG. 5B. In this set-up, the signals from the oscillator are connected between output connections 62A and 62B. This means that the RF signal is applied between the two jaw members 160 and 162 (via rods 166 and 184). At the same time the controller sends a signal to the voltage threshold detector 68 to set the peak output voltage limit to a relatively lower "coagulating" level, again as more particularly described in EP 0754437. In "coag" mode, the output from the generator is a relatively lower voltage, with a corresponding relatively higher current, and the impedance offered by the capacitor 69 is sufficient to maintain a potential difference between the output connections 62A and 62B. The capacitor 69 therefore allows sufficient voltage differential between the coagulating electrodes (160 and 162) to permit the coagulation of tissue to be performed.

It will be noted that in FIGS. 5A and 5B, only one switching element is required, with the connection between the generator and output connection 62A being maintained for both cutting and coagulation. The use of the capacitor 69 therefore simplifies the switching required, and/or frees up additional switching capability within the generator for use in other circumstances. It will also be appreciated that, although the capacitor 69 is shown in FIGS. 5A and 5B as being a part of the generator 10, it may alternatively be provided as a part of the instrument 12. In this way, different values of capacitor can be provided for different instruments, depending on their size and configuration.

It will be seen that not only is control of the RF signal different for cutting and coagulation, but also the electrodes used to perform each operation. Cutting is performed using the relatively small cutting electrode 220, using the relatively large surface area of the jaw member 160 as the return electrode. Conversely, coagulation is performed, not using the cutting electrode, but using the first and second jaw members 160 and 162. In this way both the electrical signal and the choice of electrode can be optimized, depending on the function to be performed.

In alternative embodiments of the device of FIGS. 3 and 4, the cutting electrode 220 may be located at the tip of the jaw member 162, or even on the inside jaw face as opposed to the outside jaw face illustrated in FIG. 3. Alternatively, the cutting electrode 220 and the ceramic insulator 221 may be mounted on the jaw member 162 in a recess 223 provided thereon. This is the arrangement illustrated in FIG. 3a. The operation of the instrument will be the same, and the location of the cutting electrode may merely depend on the type of procedure undertaken.

FIGS. 6 and 7 show an alternative embodiment in which the jaw members of the device of FIG. 3 are replaced by hook electrodes. These types of instrument are particularly suited to procedures such as Prostatectomy and Nephrectomy. First and second outside hook electrodes 31 and 32 are connected to output connections 62A and 62B respectively, whilst a central cutting hook electrode 33 is connected to output connection 62C. The cutting hook electrode protrudes slightly further forward than the outside electrodes 31 and 32, as shown in FIG. 6. As before, when the instrument is to be used for cutting, the switching circuit 62 is set to the state shown in FIG. 5A, and the cutting hook electrode 33 is energised with a cutting RF signal, with one or both of the outside hook electrodes acting as the return electrode. When coagulation is desired, the switching circuit is set to the state shown in FIG. 5B such that a coagulating RF signal is supplied to both of the outside hook electrodes 31 and 32.

In further alternative embodiments of the invention, either the central cutting electrode or the outside electrodes can be made extendible and retractable, or the outside electrodes can be made jaw-like in order to spread or grasp tissue to be cut or coagulated. FIG. 7a shows a variation on the device of FIGS. 6 and 7 in which the central hook electrode 33 is movable longitudinally with respect to the outside electrodes 31 and 32. In FIG. 7a the central electrode is shown retracted behind the outside electrodes, such as would be the case when coagulating using the outside electrodes or cutting by pulling the tissue towards the central cutting electrode 33.

In a further embodiment, illustrated in FIGS. 8 to 10, a central extendible hook electrode 40 is provided between stationary outside electrodes 41 and 42. In its retracted position, shown in FIG. 8, the central electrode protrudes only slightly beyond the outside electrodes 41 and 42. In this position, the instrument may be used as a tissue cutter, with the central electrode being supplied with a cutting RF signal from the generator 10, and one or both of the outside electrodes acting as return electrodes. The central electrode may also be extended, as shown in FIG. 10, and then retracted to hold tissue in the gap 43 created between the central hook electrode 40 and the outside electrodes 41 and 42. By supplying a coagulating RF signal to the outside electrodes (the switching circuit connecting the oscillator 60 to the output connections 62A and 62B as previously described), the tissue held in the gap 43 can be coagulated or desiccated. Alternatively, a cutting RF signal is supplied to the central hook electrode 40 (the switching circuit connecting the oscillator 60 to the output connections 62A and 62C), and the electrode 40 is retracted in order to cut through the tissue in the gap 4.

Referring to FIG. 11A, an arrangement is shown in which, in addition to the 2.2 nF capacitor 69 described previously between output connections 62A and 62B, an additional capacitor 73 is provided between output connections 62B and 62C. The value of this additional capacitor 73 is less than that for capacitor 69, typically 1.1 nF. The effect of this additional capacitor is as follows. When the switching circuit is as shown in FIG. 11A, the output stage of the generator is primarily connected between output connections 62A (and hence one of the coagulation electrodes) and 62C (and hence the cutting electrode). The relatively high potential difference between the cutting electrode and one or both of the coagulating electrodes will be such that the cutting of tissue can occur. However, the linking of the three electrodes by the capacitors 69 and 73 will have the effect that a relatively low potential difference will also be generated between output connections 62A and 62B (and hence the two coagulation electrodes). This will mean that as cutting of tissue is taking place, the tissue will simultaneously also be coagulated by the two coagulation electrodes. This simultaneous cutting and coagulation is an alternative to the sequential cutting and coagulation discussed previously. In FIG. 11B, the switching circuit is arranged such that the output stage of the generator is primarily connected between output connections 62A and 62B (and hence the two coagulation electrodes). This is the arrangement for the "coagulation only" setting of the device. The effect of the additional capacitor 73 will be that coagulation will occur between all three electrodes, with the cutting electrode becoming an additional coagulation electrode in the setting of FIG. 11B.

More generally, it will be appreciated that other embodiments of electrode, both stationary and movable, can be envisioned without departing from the scope of the present invention. By employing three or more electrodes and switching between them, and also adjusting the RF signal depending on which electrodes are being employed at any one time, the electrosurgical signal and the electrode configuration can be matched to optimum effect.

What is claimed is:

1. An electrosurgical system including a generator for generating radio frequency power, and an electrosurgical instrument including at least three electrodes, the generator comprising (i) a radio frequency output stage having at least a pair of radio frequency output lines, (ii) a power supply coupled to the output stage for supplying power to the output stage, (iii) a controller capable of varying a radio frequency signal supplied to the radio frequency output lines, and (iv) a switching circuit having at least three output connections each in electrical connection with a respective one of the at least three electrodes, and operable to vary the connections between the radio frequency output lines and the three or more output connections, the system further including a switching device operable to send a signal to the switching circuit within the generator in order to vary the electrode or electrodes to which radio frequency power is supplied, the switching device also causing a signal to be sent to the controller such that the radio frequency signal supplied to at least one of the three or more output connections vanes depending on the electrode or electrodes to which radio frequency power is supplied, one arrangement of the switching circuit being such that one of the electrodes has no direct connection to the output stage of the generator and is connected via a capacitor to another of the electrodes.

2. A system according to claim 1, wherein the capacitor has a value of between 1 and 10 nF.

3. A system according to claim 1, wherein the controller automatically adjusts the radio frequency power supplied to at least one of the at least three output connections to limit the peak generator output voltage to at least a first value when a first combination of electrodes is selected by the switching circuit, and to at least a second value when a second combination of electrodes is selected by the switching circuit.

4. A system according to claim 1, wherein two of the at least three electrodes are in the form of jaws adapted to grasp tissue therebetween.

5. A system according to claim 4, wherein the third electrode is mounted on one of the jaws, separated therefrom by an insulating member.

6. A system according to claim 5, wherein the third electrode is mounted on an external face of one of the jaws.

7. A system according to claim 5, wherein the third electrode is mounted on an internal face of one of the jaws.

8. A system according to claim 5, wherein the third electrode is mounted at the tip of one of the jaws.

9. A system according to claim 1, wherein at least one of the electrodes is in the form of a hook.

10. A system according to claim 9, wherein at least one hook electrode extends distally beyond the other electrodes.

11. A system according to claim 10, wherein there is a centrally positioned electrode extending distally beyond the other electrodes.

12. A system according to claim 9, wherein at least three of the electrodes are in the form of a hook.

13. A system according to claim 1, wherein at least one of the electrodes is longitudinally movable such that it can be extended and retracted with respect to the other electrodes.

14. A system according to claim 13, wherein the longitudinally movable electrode is positioned centrally between the other electrodes.

15. A system according to claim 1, wherein the arrangement is such that the output stage supplies radio frequency power to at least three electrodes simultaneously, the output voltage being limited to a first peak value between a first combination of electrodes, and to a second peak value between a second combination of electrodes.

16. A system according to claim 15, wherein, in that in a first arrangement of the switching circuit, a first one of the electrodes has no direct connection to said output stage of the generator and is connected via a capacitor to another of the electrodes, and, in a second arrangement of the switching circuit, a second one of the electrodes has no direct connection to said output stage of the generator and is connected via a capacitor to another of the electrodes.

* * * * *